United States Patent
Kavanagh et al.

(10) Patent No.: US 12,186,481 B2
(45) Date of Patent: Jan. 7, 2025

(54) SYSTEMS AND METHODS FOR PROVIDING INTERMITTENT HYPOXIC TRAINING

(71) Applicant: FFK2011 LTD., Manchester (GB)

(72) Inventors: Christopher Alan Kavanagh, Wellington (NZ); Celia Frances Kavanagh, Wellington (NZ)

(73) Assignee: FFK2011 LTD., Radcliffe (GB)

( * ) Notice: Subject to any disclaimer, the term of this patent is extended or adjusted under 35 U.S.C. 154(b) by 940 days.

(21) Appl. No.: 17/268,382

(22) PCT Filed: Aug. 14, 2019

(86) PCT No.: PCT/IB2019/056884
§ 371 (c)(1),
(2) Date: Feb. 12, 2021

(87) PCT Pub. No.: WO2020/035796
PCT Pub. Date: Feb. 20, 2020

(65) Prior Publication Data
US 2021/0196911 A1 Jul. 1, 2021

Related U.S. Application Data

(60) Provisional application No. 62/718,345, filed on Aug. 13, 2018.

(51) Int. Cl.
*A61M 16/00* (2006.01)
*A61M 16/20* (2006.01)
*A61M 16/10* (2006.01)

(52) U.S. Cl.
CPC .... *A61M 16/0045* (2013.01); *A61M 16/0063* (2014.02); *A61M 16/024* (2017.08);
(Continued)

(58) Field of Classification Search
CPC .......... A61M 16/0045; A61M 16/0063; A61M 16/024; A61M 16/202; A61M 16/1055;
(Continued)

(56) References Cited

U.S. PATENT DOCUMENTS 5,850,833 A 12/1998 Kotliar
2005/0247311 A1* 11/2005 Vacchiano ........ A61M 16/1015
128/203.12
(Continued)

FOREIGN PATENT DOCUMENTS

DE 102012010806 12/2013
EP 1721629 A1 11/2006
WO WO-2007086766 A1 * 8/2007 ........ A61M 16/0075

OTHER PUBLICATIONS

International Preliminary Report on Patentability; PCT/IB2019/056884; Feb. 16, 2021.

*Primary Examiner* — Justine R Yu
*Assistant Examiner* — Matthew R Moon
(74) *Attorney, Agent, or Firm* — Haynes and Boone, LLP

(57) ABSTRACT

A hypoxic training system is provided that dynamically adjusts the oxygen ratio in the gas provided to the user during a hypoxic training session based on the blood oxygen saturation ($SPO^2$) level of the user. During a first training period, the hypoxic training system provides gas according to a first oxygen ratio. When it is determined that the $SPO^2$ level of the user has reached a target $SPO^2$ level, the hypoxic training system may provide a recovery period, during which gas according to a second oxygen ratio is provided to the user. When it is determined that the $SPO^2$ level of the user has fallen more than a predetermined threshold below the target $SPO^2$ level during the recovery period, the hypoxic training system may provide gas according to an increased first oxygen ratio during a subsequent training period.

20 Claims, 5 Drawing Sheets

(52) U.S. Cl.
CPC ....... *A61M 16/202* (2014.02); *A61M 16/1055* (2013.01); *A61M 2202/0208* (2013.01); *A61M 2205/3334* (2013.01); *A61M 2205/502* (2013.01); *A61M 2230/205* (2013.01)

(58) Field of Classification Search
CPC .. A61M 2202/0208; A61M 2205/3334; A61M 2205/502; A61M 2230/205; A61M 16/0078; A61M 2209/084; A61M 16/1005; A61M 2205/7545; A61M 2230/005; A61M 16/10; A61M 2016/1025; A61M 16/00; A61M 16/003; A61M 16/0033; A61M 16/022; B01D 2257/104; B01D 53/22; B01D 2259/4533; A63B 2213/006; A63B 2213/005; A62B 7/00; A62B 18/00
See application file for complete search history.

(56) References Cited

U.S. PATENT DOCUMENTS

| | | | | |
|---|---|---|---|---|
| 2006/0185669 | A1* | 8/2006 | Bassovitch | A61M 16/0045 |
| | | | | 128/205.26 |
| 2009/0183738 | A1* | 7/2009 | Kostin | A61M 16/0063 |
| | | | | 128/204.18 |
| 2010/0297593 | A1* | 11/2010 | Chapman | A61M 16/0075 |
| | | | | 128/203.14 |
| 2012/0090611 | A1* | 4/2012 | Graboi | A61M 16/12 |
| | | | | 128/204.23 |
| 2016/0095994 | A1 | 4/2016 | Currin et al. | |

\* cited by examiner

SYSTEMS AND METHODS FOR PROVIDING INTERMITTENT HYPOXIC TRAINING

CROSS REFERENCE TO RELATED APPLICATION

This application claims priority to PCT Application No. PCT/IB2019/056884, filed on Aug. 14, 2019, and claims the benefit of and priority to U.S. Provisional Application No. 62/718,345, filed on Aug. 13, 2018, wherein both applications are hereby incorporated by reference in their entireties.

BACKGROUND

The present specification generally relates to hypoxic training, and more specifically, to dynamically adjusting the oxygen ratio of the gas during hypoxic training to achieve and/or produce sporting, medical and therapeutic benefits.

RELATED ART

Hypoxic training involves artificially supplying a subject with hypoxic air to place a beneficial stress on the subject's pulmonary system. Generally, this type of training is applied intermittently to allow the subject to recover from the stress by breathing normoxic air. In order to artificially provide hypoxic air to the subject, a hypoxic training machine may be utilized to generate gas that has less oxygen content than normoxic air. Conventional hypoxic training machines require a nitrogen supply and provide the gas by mixing normoxic air with nitrogen. However, this method of providing the mixed gas is both inconvenient and costly. For example, nitrogen supply (e.g., in the form of nitrogen tanks) must be available in order for the hypoxic training machines to operate. Furthermore, since it is difficult to accurately control the amount of nitrogen provided to the hypoxic machines, expensive oxygen analyzer is often required to be included in these hypoxic training machines to provide feedback. As such there is a need for an improved hypoxic training system.

In addition, while studies have shown that in general, there are many benefits to hypoxic training, incorrectly configuring and using a hypoxic training machine may lead to fatigue and non-responsiveness, which may counter, or even outweigh, the benefits provided by the hypoxic training. As such, there is a need for a hypoxic training system that provides hypoxic training to user which reduces the negative side effects and increase the physical benefits of hypoxic training.

Figure 1:
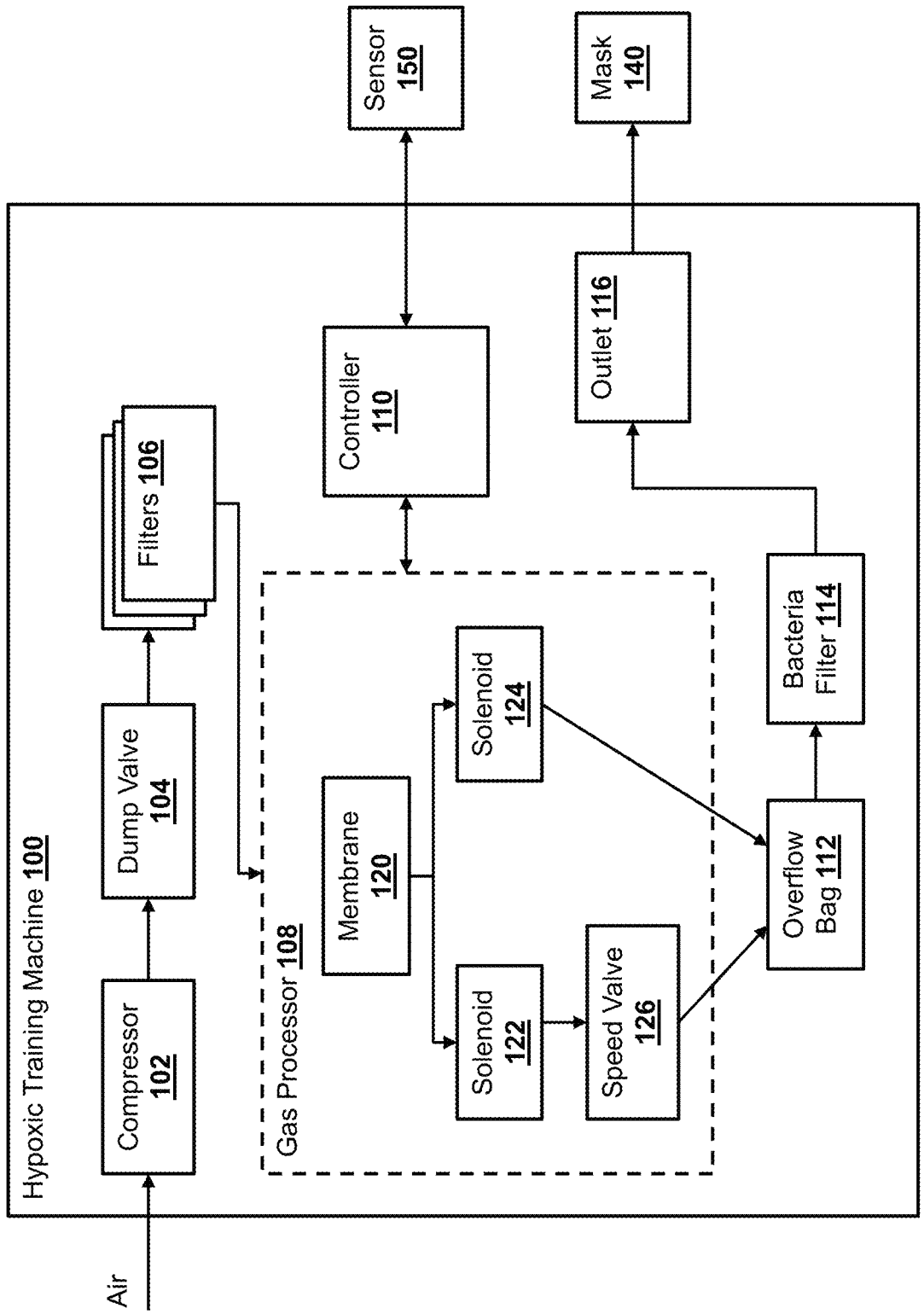
FIG. 1 is a block diagram illustrating a hypoxic training system according to an embodiment of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The present disclosure describes methods and systems for providing intermittent hypoxic training for providing sporting, medical and therapeutic benefits. In one aspect of the disclosure, a hypoxic training system that does not require a nitrogen supply is presented. The hypoxic training system includes a gas processor for generating (producing) a gas according to a desired oxygen ratio. In some embodiments, the gas processor includes a membrane and one or more solenoids. As gas (e.g., air) passes through the membrane, the membrane is configured to reduce the oxygen content of the gas to generate processed gas, such that the processed gas has less oxygen content (e.g. a lower oxygen ratio in the filtered gas) than the unprocessed gas that enters the membrane. Each of the one or more solenoids can be controlled to open at one or more levels. The different opening levels of the one or more solenoids create different back pressures for the membrane, resulting in different oxygen content being filtered out in the membrane.

In some embodiments, the gas processor may also include a speed valve for controlling the speed of the flow of the gas coming out of the one or more solenoids. By controlling the speed of the flow of the gas coming out of the one or more solenoids, the speed valve may beneficially be used to regulate the back pressure for the membrane to further enhance the precision of the oxygen ratio in the processed gas.

As such, the oxygen ratio of the processed gas can be precisely controlled by controlling the openings of the one or more solenoids and the speed valve. The processed gas is then fed through an outlet junction to a mask for use by a user.

In some embodiments, the hypoxic training system may include a controller for controlling the gas processor. Specifically, the controller may dynamically adjust the oxygen ratio in the processed gas by controlling the openings of the one of more solenoids and/or the setting of the speed valve. For example, the controller may control the gas processor to provide the processed gas at a first oxygen ratio during a training period and may control the gas processor to provide the processed gas at a second oxygen ratio during a recovery period.

By using the gas processor as disclosed herein, the hypoxic training machine advantageously eliminates the need of a nitrogen supply. Furthermore, the use of the one or more solenoids and the membrane enables the hypoxic training machine to control the oxygen ratio in the output gas more precisely.

In some embodiments, the hypoxic training system may also include a compressor in the upstream of the gas mixer. The compressor compresses an input gas (e.g., air) before providing the compressed gas to the gas processor. In some embodiments, the compressor compresses the input gas to a compressed gas having a pressure of approximately 7 bar.

In some embodiments, the hypoxic training system may include one or more filters disposed in the upstream of the gas processor, and configured to filter out impurities, such as dust and pollen, in the compressed gas before providing the compressed gas to the gas processor.

In some embodiments, the hypoxic training system may include an overflow bag in the downstream of the gas processor to prevent over-breathing. Over-flow of the processed gas not inhaled by the user can be collected by the overflow bag.

In another aspect of the disclosure, a hypoxic training system is provided that dynamically adjusts the oxygen ratio in the processed gas provided to the user during a hypoxic training session based on the blood oxygen saturation ($SPO^2$) level of the user in a manner that reduces fatigue in the hypoxic training session. In some embodiments, the hypoxic training system is configured to provide hypoxic air intermittently to allow a user to recover from the stress by breathing normoxic air. In other words, the hypoxic training system may provide one or more recovery periods between training periods during a hypoxic training session. During a training period, the hypoxic training system may be configured to provide gas according to a first oxygen ratio. In some embodiments, the first oxygen ratio corresponds to a hypoxic air oxygen ratio that is predetermined for the hypoxic training session. As an example, the oxygen ratio in normoxic air (air at approximately sea-level altitude) may be between 20% and 22%. The first oxygen ratio may be determined to be between 7% and 19%, inclusively. In one example, the first oxygen ratio may be determined to be 11%.

As the user intakes the gas having the first oxygen ratio provided by the hypoxic training system during the first training period, the $SPO^2$ level of the user may begin to fall from the normal $SPO^2$ level (e.g., 100%). For example, the $SPO^2$ level of the user may fall from 100% to 95%, then to 92%, or even lower. During each training session, a target $SPO^2$ level may be determined for the user to reach. Having the user reach the target $SPO^2$ level during the training period will provide and/or enhance the benefits of a hypoxic training. Different target $SPO^2$ levels may be determined for different users. In some embodiments, the target $SPO^2$ level may be determined for a user based on the physical condition of the user. An example target $SPO^2$ level may be 90% for the user. While reaching the target $SPO^2$ level may provide health benefits to the user, having the $SPO^2$ level falling too low may cause harm (e.g., fatigue) to the user, which as mentioned above, may even outweigh the benefits of the hypoxic training.

As such, the hypoxic training system may be configured to monitor the $SPO^2$ level of the user during a first training period, while processed gas having the first oxygen ratio is provided to the user. For example, the controller may obtain a blood oxygen saturation ($SPO^2$) level of the user (e.g., based on a reading from a pulse oximeter) while the user is using the hypoxic training machine during the hypoxic training session. The hypoxic training system may monitor the $SPO^2$ level of the user to determine whether the $SPO^2$ level of the user has reached (fallen to) the predetermined $SPO^2$ level (e.g., the target $SPO^2$ level).

When the hypoxic training system determines that the $SPO^2$ level of the user has reached (fallen to) the target $SPO^2$ level (e.g., 90%), the hypoxic training system may be configured to provide a recovery period, during which gas according to a second oxygen ratio is provided to the user. In some embodiments, the second oxygen ratio corresponds to a normoxic air oxygen ratio. For example, the second oxygen ratio may be determined to be 20.9%. Providing gas according to the second oxygen ratio to the user may cause the $SPO^2$ level of the user to rise (e.g., so that the body of the user can recover). However, as the body may not react instantaneously to intake of normoxic air, the $SPO^2$ level of the user may continue to drop at the beginning of the recovery period before $SPO^2$ level of the user rises back up again.

As such, the hypoxic training system may continue to monitor the $SPO^2$ level of the user during the recovery period. When the hypoxic training system determines that the $SPO^2$ level of the user has fallen more than a predetermined threshold below the target $SPO^2$ level (at a level which may harm the user), the hypoxic training system may adjust the first oxygen ratio. In some embodiments, the predetermined threshold is a percentage within a range between 1% and 4%, inclusively. In some embodiments, the predetermined threshold is a percentage within a range between 1.5% and 3%, inclusively. Specifically, the predetermined threshold is approximately 2% (e.g., within 20% deviation from 2%). Thus, using the example above where the target $SPO^2$ level is 90%, when the hypoxic training system determines that the $SPO^2$ level has reached or fallen below 88%, the hypoxic training system adjusts the first oxygen ratio. It has been observed, through experiments and studies performed by the inventors, that (1) dynamically adjusting the oxygen ratio for the gas provided during training periods and (2) dynamically adjusting the duration of the training periods based on physical condition (e.g., the $SPO^2$ level) of the user using the techniques disclosed herein dramatically increases the benefits (e.g., physiological and health benefits, regeneration and remodeling of neuro-circuitry, positive shift in dopamine and serotonin metabolism in the central nervous system, improves cognition and neuroplasticity, improve physical, respiratory, motor function, reduces inflammation in the body, etc.) that the user receives from the hypoxic training and substantially reduces negative side effects (e.g., fatigue, non-responders, etc.) to the user than other conventional hypoxic training methods.

In some embodiments, adjusting the first oxygen ratio comprises increasing the first oxygen ratio by a predetermined value. For example, the first oxygen ratio may be increased by a value within a range between 0.2% and 1.5%, inclusively. In some embodiments, the first oxygen ratio may be increased by a value within a range between 0.3% and 0.7%, inclusively. In some embodiments, the first oxygen ratio may be increased by approximately 0.5% (e.g., within 20% deviation from 0.5%). Thus, the hypoxic training system may adjust the first oxygen ratio from 11% to 11.5%. It has been observed, through experiments and studies performed by the inventors, that increasing the first oxygen ratio for the gas provided during a subsequent training at the value described above provides a substantially larger reduction of negative side effects (e.g., fatigue) to the user than any other increase.

During the recovery period, when the hypoxic training system determines that the $SPO^2$ level of the user has risen to (reached) a target recovery $SPO^2$ level that is above the target $SPO^2$ level (e.g., 92%), the hypoxic training system may then be configured to provide a second training period, during which gas according to the adjusted first oxygen ratio (e.g., 11.5%) is provided to the user. By adjusting the oxygen ratio of the gas provided in a training period based on the $SPO^2$ level of the user detected in a previous recovery period, the hypoxic training system advantageously reduces the negative side effect, such as fatigue, of the hypoxic training, which increases the benefits of the training to the user.

As discussed above, the hypoxic training system may be configured to monitor the $SPO^2$ level of the user during the first training period to determine whether the $SPO^2$ level of the user has fallen to (reached) the target $SPO^2$ level (e.g., 90%) determined for the user. There are instances where the $SPO^2$ level of the user may never fall to (reach) the target $SPO^2$ level. Failing to reach the target $SPO^2$ level may indicate that the first oxygen ratio used in the training period is not low enough for the user. As such, in some embodiments, the hypoxic training system may determine whether a predetermined amount of time has passed since the initiation of the first training period. For example, the hypoxic training system may start a timer at the beginning of a training period. In some embodiments, the predetermined amount of time may be between 80 seconds and 106 seconds, inclusively. In some embodiments, the predetermined amount of time may be between 90 seconds and 100 seconds. In one example, the amount of time may be 96 seconds.

When the hypoxic training system determines that the predetermined amount of time has passed and the $SPO^2$ level of the user still has not reached the target $SPO^2$ level, the hypoxic training system may be configured to reduce the first oxygen ratio by a reduction amount. In some embodiments, the reduction amount may be a value within a range between 0.3% and 1.5%, inclusively. In some embodiments, the first oxygen ratio may be increased by approximately 0.5% (e.g., within 20% deviation from 0.5%). Thus, the hypoxic training system may adjust the first oxygen ratio from 11% to 10.5%. It has been observed, through experiments and studies conducted by the inventors, that reducing the oxygen ratio in the gas provided to the user at the reduction amount after the predetermined amount of time has passed without reaching the target $SPO^2$ level provides substantially more benefits to the user than at other reduction amount and waited for other amounts of time.

FIG. 1 illustrates a schematic of a hypoxic training machine 100 according to one embodiment of the disclosure. The hypoxic training machine 100 includes a compressor 102, a dump valve 104 downstream to the compressor 102, one or more filters 106 downstream to the dump valve 104, a gas processor 108 downstream to the filters 106, a controller 110 communicatively coupled with the gas processor 108, an overflow bag 112 downstream to the gas processor 108, a filter 114 downstream to the overflow bag 112, and an outlet 116 downstream to the filter 114. As shown, the controller 110 may be communicatively coupled with a sensor 150, which may or may not be part of the hypoxic training machine 100. Furthermore, the outlet 116 is connected to a mask 140, which may or may not be part of the hypoxic training machine 100. The compressor 102, the dump valve 104, the filters 106, the gas processor 108, the overflow bag 112, the bacteria filter 114, and the outlet 116 may be connected with each other through one or more airways (e.g., pipes).

In some embodiments, the hypoxic training machine 100 may include an inlet (not shown) to allow air to enter into the hypoxic training machine 110. The air that enters the hypoxic training machine 110 is guided by the inlet to the compressor 102, which compresses the air into compressed air. In some embodiments, the compressor 102 may be configured to compress air from the atmospheric pressure of approximately 1 bar to 7 bar. The compressed air is then guided (e.g., via an airway) to the dump valve 104. The dump valve 104 may have an open state or a close state. During normal operation of the hypoxic training machine 100, the dump valve 104 is remained at a close state, which allows the compressed air to pass through the dump valve 104 and through the filters 106. However, the dump valve 104 can be opened for clearing the airways within the hypoxic training machine 100.

As such, during normal operation of the hypoxic training machine 100, the compressed air may be guided (e.g., by an airway) to the one or more filters 106. The one or more filters 106 may be configured to filter out impurities such as dust in the compressed air. Example filters that can be used to implement the filters 106 includes micron filter having ¼ BSP, 0.1 BSP, 0.5 BSP, 0.8 BSP, 1 BSP, 2 BSP, or 5 BSP.

After going through the filters 106, the compressed air is then guided to the gas processor 108 (e.g., via an airway). As shown, the gas processor 108 may include a membrane 120, solenoids 122 and 124, and a speed valve 126. The membrane 120 is made of a material (e.g., a fiber) that is configured to reduce the oxygen content of the gas to generate processed gas, such that the processed gas has less oxygen content (e.g. a lower oxygen ratio in the filtered gas) than the unprocessed gas that enters the membrane 120. An example of the membrane 120 that is used in the hypoxic training machine 100 can be found in U.S. Pat. No. 7,717,983 titled "Air Separation Module with Load Carrying Center Tube" to Semmere et al., issued on May 18, 2010, which is incorporated in its entirety herein by reference. For example, without any back pressure, when air with a normal oxygen ratio (e.g., 20.9% oxygen ratio) passes through the membrane 120, the oxygen ratio of the gas that exits the membrane 120 may be reduced to an oxygen ratio as low as 4%.

The membrane 120 is connected to the solenoids 122 and 124, for example, via one or more airways, such that the gas coming out of the membrane 120 is diverted to two different paths. Each of the paths guides the gas to one of the solenoids 122 and 124. Each of the solenoids 122 and 124 can be controlled to open at one or more levels (e.g., 26 different levels). Configuring the solenoids 112 and 124 to operate at the different opening levels creates different back pressures for the membrane 120, resulting in different oxygen content being filtered out in the membrane 120.

In some embodiments, the speed valve is disposed downstream of one of the solenoids (e.g., the solenoid 122), and is configured to control the speed of the flow of the gas coming out of the solenoid 122. By controlling the speed of the flow of the gas coming out of the solenoid 122, the speed valve 126 may beneficially be used to regulate the back pressure for the membrane 120 to further enhance the precision of the oxygen ratio in the processed gas.

As shown, in some embodiments, the gas processor 108 may be communicatively coupled with a controller 110. The controller 110 may be implemented as any appropriate circuitry or device (e.g., a processor, microcontroller, a printed circuit board (PCB), an application specific integrated circuit (ASIC), a field-programmable gate array (FPGA), or other programmable or configurable logic devices) that is configured (e.g., by hardware configuration, software instructions, or a combination of both) to perform various operations for the hypoxic training machine 100 as described herein.

In some embodiments, the controller 110 may be configured to control the oxygen ratio in the gas coming out of the gas processor 108. For example, the controller 110 of some embodiments may dynamically control the oxygen ratio in the gas coming out of the gas processor 108 by adjusting the opening levels of the solenoids 122 and 124 and/or by configuring the speed valve 126 to adjust the speed of the gas coming through the speed valve 126. Thus, the controller may control the gas processor to provide the processed gas at a first oxygen ratio during a training period and may control the gas processor to provide the processed gas at a second oxygen ratio during a recovery period.

In some embodiments, the controller 110 is communicatively coupled to the sensor 150. The sensor 150, in some embodiments, may be a pulse oximeter that is configured to detect a $SPO^2$ level of a user who is using the hypoxic training machine 100. In some embodiments, the controller 110 may be configured to dynamically adjust the oxygen ratio in the gas that is output by the hypoxic training machine 100 by controlling the gas processor 108 based on the detected $SPO^2$ level of the user.

The processed gas coming out of the speed valve 126 and the solenoid 124 are joined and then guided (e.g., via an airway) pass the overflow bag 112. The overflow bag 112 may be implemented as a container for collecting gas that is not used (intake) by the user of the hypoxic training machine 100, in order to prevent over-breathing of the user. An example overflow bag 112 may have a size to hold three liters of gas. The gas, once guided passed the overflow bag 112, is guided to the bacteria filter 114. The bacteria filter 114 may be configured to filter out various bacteria contained in the processed gas. An example bacteria filter may include a high efficiency particulate air (HEPA) filtration system. The processed gas is then guide to the outlet 116, which may then be led to the mask 140, which is attached to the user when the user is using the hypoxic training machine 100.

Figure 2:
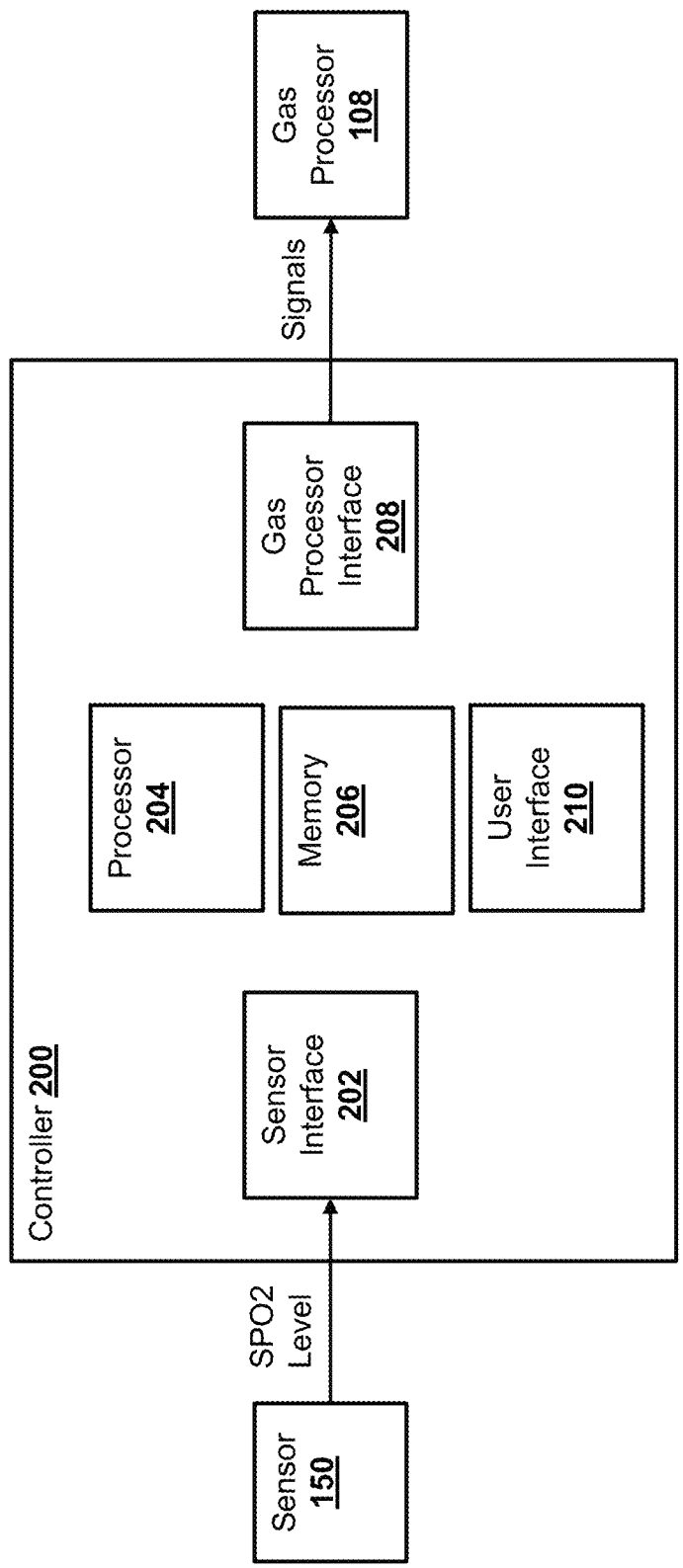
FIG. 2 is a block diagram illustrating a controller for a hypoxic training system according to an embodiment of the present disclosure.

FIG. 2 illustrates a schematic of a controller 200 according to one embodiment of the disclosure. In some embodiments, the controller 200 may be implemented as the controller 110. As shown, the controller 200 includes a sensor interface 202, a processor 204, a memory 206, a gas processor interface 208, and a user interface 210. The sensor interface 202 is configured to obtain $SPO^2$ data from the sensor 150. The memory 206 may be implemented as a non-transitory memory such as random-access memory (RAM) or a flash drive. The memory 206 may store software instructions that when executed by the processor 204 perform various functions for the controller 200. For example, the processor 204 may generate one or more signals corresponding to adjusting the oxygen ratio of the gas provided by the hypoxic training machine 100 based on the $SPO^2$ data obtained from the sensor 105 via the sensor interface 202, and may transmit the signals to the gas processor 108 via the gas processor interface to dynamically control the gas processor based on the $SPO^2$ data obtained from the sensor 150.

Figure 3:
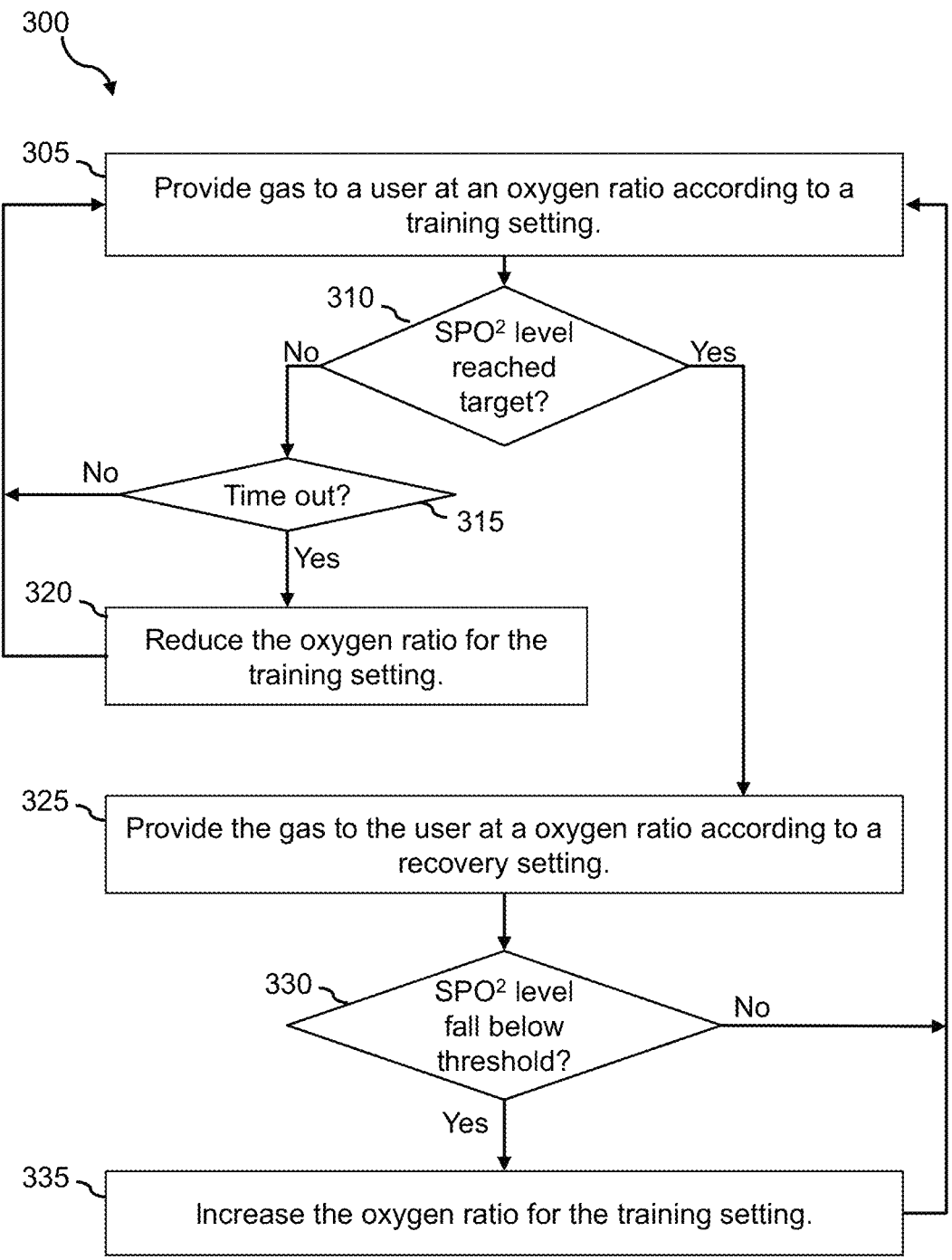
FIG. 3 is a flowchart showing a process of dynamically adjusting the oxygen ratio in a gas based on a blood oxygen saturation level of a subject according to an embodiment of the present disclosure.

FIG. 3 is a flow chart illustrating a process 300 for dynamically adjusting the oxygen ratio of the gas provided to a user of a hypoxic training machine based on a $SPO^2$ level of the user according to various embodiments of the disclosure. In some embodiments, the process 300 may be performed by the controller 110 and/or the controller 200. The process 300 begins by providing (at step 305) gas to a user at an oxygen ratio according to a training setting. For example, the controller 110 and/or the controller 200 may configure the gas processor 108 to provide, to the mask 140, gas at a first oxygen ratio during a first training period. As discussed above, the first oxygen ratio may be sufficiently lower from the oxygen ratio of normoxic air (at approximately 20.9%), but high enough to not induce injury or physical harm to the user. For example, the first oxygen ratio may be within a range between 7% and 19%, inclusively. In one example, the first oxygen ratio may be 11%.

In some embodiments, the controller 110 and/or the controller 200 may configure the gas processor 108, by adjusting the opening levels of one of more of the solenoids 122 and 124 and/or adjusting the configuration of the speed valve 126, to produce gas having the first oxygen ratio.

While the hypoxic training machine 100 is providing gas at the first oxygen ratio to the user, the controller 110 and/or the controller 200 may obtain $SPO^2$ data from the sensor 150 in order to monitor the $SPO^2$ level of the user. For example, the controller 110 and/or the controller 200 may periodically (e.g., every second, every 2 seconds, every 5 seconds, etc.) pull $SPO^2$ data from the sensor 150 to determine whether the $SPO^2$ level of the user has fallen to (reached) a target $SPO^2$ level. As discussed above, the user's $SPO^2$ level under normal circumstances (not deprived of oxygen) may be at a normal $SPO^2$ level (e.g., 100%). A target $SPO^2$ level may be determined for the user during each training session. The goal during the hypoxic training session is for the user to reach the target $SPO^2$ level. Having the user reach the target $SPO^2$ level during the training period may provide and/or enhance the benefits of a hypoxic training. The target $SPO^2$ level may be determined differently for different users. In some embodiments, the target $SPO^2$ level may be determined for a user based on the physical condition of the user. For example, a target $SPO^2$ level for a user may be within the range of 80% and 98%. An example target $SPO^2$ level may be 90% for the user. In some embodiments, the controller 110 and/or the controller 200 may provide an interface (e.g., via the user interface 210) to enable the user or a technician for the hypoxic training machine 100 to input a target $SPO^2$ level for the user.

The process 300 then determines (at step 310) whether the target $SPO^2$ level has been reached. For example, the controller 110 and/or the controller 200 may monitor the $SPO^2$ level of the user throughout the first training period (e.g., by periodically pulling the $SPO^2$ data from the sensor 150 as discussed herein), and determine whether the $SPO^2$ level of the user has fallen to (reached) the target $SPO^2$ level. Once the hypoxic training machine 100 begins to provide gas at the first oxygen ratio to the user, the $SPO^2$ level of the user should be slowly falling. For example, the $SPO^2$ level of the user may fall from 100% to 98%, and then to 97% and so forth. In some embodiments, the controller 110 and/or the controller 200 may continue to monitor the $SPO^2$ level of the use as the $SPO^2$ level of the user continues to fall.

The $SPO^2$ level of the user may never reach the target $SPO^2$ level based on the first oxygen ratio. For example, the physical condition of the user may be stronger than expected, and the first oxygen ratio may not be low enough to cause the $SPO^2$ level of the user to fall to the target $SPO^2$ level. Thus, when the $SPO^2$ level of the user has not reached the target $SPO^2$ level after the gas at the first oxygen ratio has been provided to the user for a predetermined amount of time, the controller 110 and/or the controller 200 may adjust the first oxygen ratio (e.g., reduce the first oxygen ratio). The predetermined amount of time should be set sufficiently long to allow time for the user's body to react to the gas provided by the hypoxic training machine 100 (e.g., to allow time for the $SPO^2$ level of the user to fall to the target $SPO^2$ level), but not too long which may reduce the efficiency of the hypoxic training provided to the user. It has been observed, through experiments and studies by the inventors, that reducing the first oxygen ratio for the gas provided in the first training period after the gas is provided to the user for a time between 66 seconds and 126 seconds (and the $SPO^2$ level still has not reached the target $SPO^2$ level) can be beneficial to the user. Preferably, the hypoxic training machine 100 may be configured to reduce the first oxygen ratio after the gas has been provided to the user for a time between 90 seconds and 100 seconds, and the $SPO^2$ level still has not reached the target $SPO^2$ level. Even more preferably, the hypoxic training machine 100 may be configured to reduce the first oxygen ratio after the gas has been provided to the user for approximately 96 seconds (e.g., within 20% deviation from 96 seconds), and the $SPO^2$ level still has not reached the target $SPO^2$ level.

As such, when it is determined that the $SPO^2$ level of the user has not reached the target $SPO^2$ level, the process 300 may determine (at step 315) whether the gas at the first oxygen ratio has been provided to the user for the predetermined amount of time. For example, each time the controller 110 and/or the controller 200 pulls the $SPO^2$ data from the sensor 150, the controller 110 and/or the controller 200 may determine whether the $SPO^2$ level of the user, indicated by the $SPO^2$ data, has reached (or fallen to) the target $SPO^2$ level. If the $SPO^2$ level of the user is determined to not have reached the target $SPO^2$ level, the controller 110 and/or the controller 200 may determine whether the gas at the first oxygen ratio has been provided to the user for the predetermined amount of time. In some embodiments, the controller 110 and/or the controller 200 may initiate a timer at the beginning of the first training period (e.g., when the gas at the first oxygen ratio has first been introduced to the user). Each time the controller 110 and/or the controller 200 pulls the $SPO^2$ data from the sensor 105, the controller 110 and/or the controller 200 may check the timer to determine whether the predetermined amount of time (e.g., 96 seconds) has passed.

If the predetermined amount of time has not passed, the process 300 reverts to step 305 to continue to provide the gas at the first oxygen ratio to the user. On the other hand, if it is determined that the predetermined amount of time has passed, the process 300 reduces (at step 320) the first oxygen ratio for the first training period. For example, when the controller 110 and/or the controller 200 determines that the timer has reached the predetermined time value (e.g., 96 seconds), the controller 110 and/or the controller 200 may adjust the first oxygen ratio by reducing the first oxygen ratio by a predetermined amount, and may transmit a signal to the gas processor 108 to provide gas at the reduced first oxygen ratio of the gas.

The first oxygen ratio needs to be reduced by an amount sufficient to cause the $SPO^2$ level of the user to fall to (reach) the target $SPO^2$ level, but not too low to physical harm the user's body. It has been observed, through experiments and studies by the inventors, that reducing the first oxygen ratio by a value within a range between 0.3% and 1.5% provides substantially more benefits to the user than values outside of the range. Preferably, the first oxygen ratio is reduced by approximately 0.5% (e.g., within 20% deviation from 0.5%), as it has been observed that reducing the first oxygen ratio by approximately 0.5% provides substantially more benefits to the user than other values. As such, using the example given above, the controller 110 and/or the controller 200 may reduce the first oxygen ratio from 11% to 10.5%. The controller 110 and/or the controller 200 may then transmit a signal to the gas processor 108 to adjust the opening levels of the solenoid 122 and 124, and the configuration of the speed valve 126 in a manner such that the gas outputted by the gas processor 108 has the reduced first oxygen ratio (e.g., 10.5%).

After reducing the first oxygen ratio, the process 300 reverts back to step 305 to provide the gas at the reduced first oxygen ratio to the user. In some embodiments, the controller 110 and/or the controller 200 may also reset the timer, and continue to monitor the $SPO^2$ level of the user. When it is determined that after the predetermined amount of time (e.g., 96 seconds) has passed again since the gas at the reduced first oxygen ratio has been provided to the user and the $SPO^2$ level of the user still has not reached the target $SPO^2$ level, the controller 110 and/or the controller 200 may again reduce the first oxygen ratio (e.g., from 10.5% to 10%), and may continue to reduce the first oxygen ratio until it is determined that the $SPO^2$ level of the user has reached the target $SPO^2$ level.

When the process 300 determines at the step 310 that the $SPO^2$ level of the user has reached the target $SPO^2$ level determined for the user, the process 300 provides (at step 325) gas to the user at a second oxygen ratio according to a recovery setting. For example, when the controller 110 and/or the controller 200 determines that the $SPO^2$ level of the user has reached the target $SPO^2$ level (e.g., the $SPO^2$ data obtained from the sensor 150 indicates that the $SPO^2$ level of the user is at or below the target $SPO^2$ level), the controller 110 and/or the controller 200 may control the gas processor 108 to change from a training mode to a recovery mode, where gas at the second oxygen ratio is provided to the user during the recovery period. In order to reduce the side effect of fatigue, once the target $SPO^2$ level is reached, a recovery period is provided to the user during which normoxic air is provided to the user. As such, the second oxygen ratio may correspond to an oxygen ratio in normoxic air (e.g., approximately 20.9%).

It has been observed that the $SPO^2$ level of the user may continue to fall, at least initially for a period of time, even after the hypoxic training machine 100 has shifted from the training mode to the recovery mode, where gas at the second oxygen ratio (e.g., normoxic air) is being provided, before the $SPO^2$ level rises back up. While reaching the target $SPO^2$ level may provide health benefits to the user, having the $SPO^2$ level falling too low may cause harm (e.g., fatigue) to the user, which as mentioned above, may even outweigh the benefits of the hypoxic training. Having the $SPO^2$ level of the user fallen too low may indicate that the first oxygen ratio provided to the user during the previous training period is too low for the user, as it may cause undesirable harm to the user's body. As such, the controller 110 and/or the controller 200 may continue to monitor the $SPO^2$ level of the user during the recovery period, and may determine to adjust (e.g., raise) the first oxygen ratio for the subsequent training period when it is determined that the $SPO^2$ level of the user has fallen too low.

It has been observed, through experiments and studies by the inventors, that the user may sustain substantially more harm to the body when the $SPO^2$ level of the user falls more than 4% below the target $SPO^2$ level. Specifically, through experiments and studies by the inventors, that the user may sustain substantially more harm to the body when the $SPO^2$ level of the user falls more than approximately 2% (e.g., within 20% deviation from 2%) below the target $SPO^2$ level. As such, in some embodiments, the controller 110 and/or the controller 200 may determine that the predetermined threshold is a value within a range between 1% and 4%. Preferably, the controller 110 and/or the controller 200 may determine that the predetermined threshold is a value within a range between 1.5% and 3%. In one example, the controller 110 and/or the controller 200 may determine that the threshold is approximately 2% (e.g., within 20% deviation from 2%). Thus, using the example discussed above where the target $SPO^2$ level is 90%, the controller 110 and/or the controller 200 may be configured to adjust the first oxygen ratio for the subsequent training period when it is determined that the $SPO^2$ level of the user has reached (fallen to or below) 88%.

Referring back to FIG. 3, the process 300 determines (at step 330) whether the $SPO^2$ level of the user reaches (falls to or below) a predetermined threshold below the target $SPO^2$ level (e.g., 88%). If it is determined that the $SPO^2$ level of the user does not reach (fall to or below) the predetermined threshold below the target $SPO^2$ level, the process 300 maintains the first oxygen ratio for the subsequent training period and reverts back to the step 305 to provide the gas at the first oxygen ratio in the subsequent training period.

On the other hand, if it is determined that the $SPO^2$ level of the user does not reach (does not fall to or below) the predetermined threshold below the target $SPO^2$ level, the process 300 increases (at step 335) the first oxygen ratio for the subsequence training period.

Different embodiments of the controller 110 and/or the controller 200 may increase the first oxygen ratio by different amounts. It has been observed, through experiments and studies conducted by the inventors, that increasing the first oxygen ratio by a value within a range between 0.3% and 1.5%, inclusively provides substantially more benefits to the user than by a value outside of the range. It has also been observed through experiments and studies conducted by the inventors, that increasing the first oxygen ratio by approximately 0.5% (e.g., within 20% deviation from 0.5%) provides substantially more benefits to the user than by other values. As such, in some embodiments, the controller 110 and/or the controller 200 may be configured to increase the first oxygen ratio by a value within a range between 0.3% and 1.5%, inclusively. Preferably, the controller 110 and/or the controller 200 may be configured to increase the first oxygen ratio by approximately 0.5% (e.g., within 20% deviation from 0.5%). Thus, using the example discussed herein where the first oxygen level is 11%, the controller 110 and/or the controller 200 may increase the first oxygen ratio from 11% to 11.5%.

The controller 110 and/or the controller 200 may end the recovery period to begin the subsequent training period upon detecting a trigger. In some embodiments, the trigger may be a time trigger. For example, the controller 110 and/or the controller 200 may initiate a timer at the beginning of the recovery period and may end the recovery period when the timer reaches a predetermined time value, such as 30 seconds. In some embodiments, the trigger may be an $SPO^2$ level of the user. For example, the controller 110 and/or the controller 200 may continue to monitor the $SPO^2$ level of the user (e.g., through $SPO^2$ data obtained from the sensor 150) through the recovery period, and end the recovery period when it is determined that the $SPO^2$ level of the user has reached a predetermined recovery $SPO^2$ level. In some embodiments, the recovery $SPO^2$ level may be a value between 1% and 3% above the target $SPO^2$ level. For example, the recovery $SPO^2$ level may be 2%. Using the example discussed herein where the target $SPO^2$ level is 90%, the controller 110 and/or the controller 200 may be configured to end the recovery period when it is determined that the $SPO^2$ level of the user has reached (risen to or above) 92%. The process 300 then reverts back to the step 305 to provide the gas at the first oxygen ratio (or the increased first oxygen ratio) in the subsequent (second) training period.

The process 300 may continue through the cycle from steps 305 through 335 until the end of the hypoxic training session for the user. By dynamically adjusting the oxygen ratio of the gas provided to the user throughout the hypoxic training session based on how the user's body react to the hypoxic training (e.g., based on the monitored $SPO^2$ level of the user), the hypoxic training machine 100 advantageously reduce the negative side effects of the hypoxic training (e.g., excessive fatigue).

Figure 4:
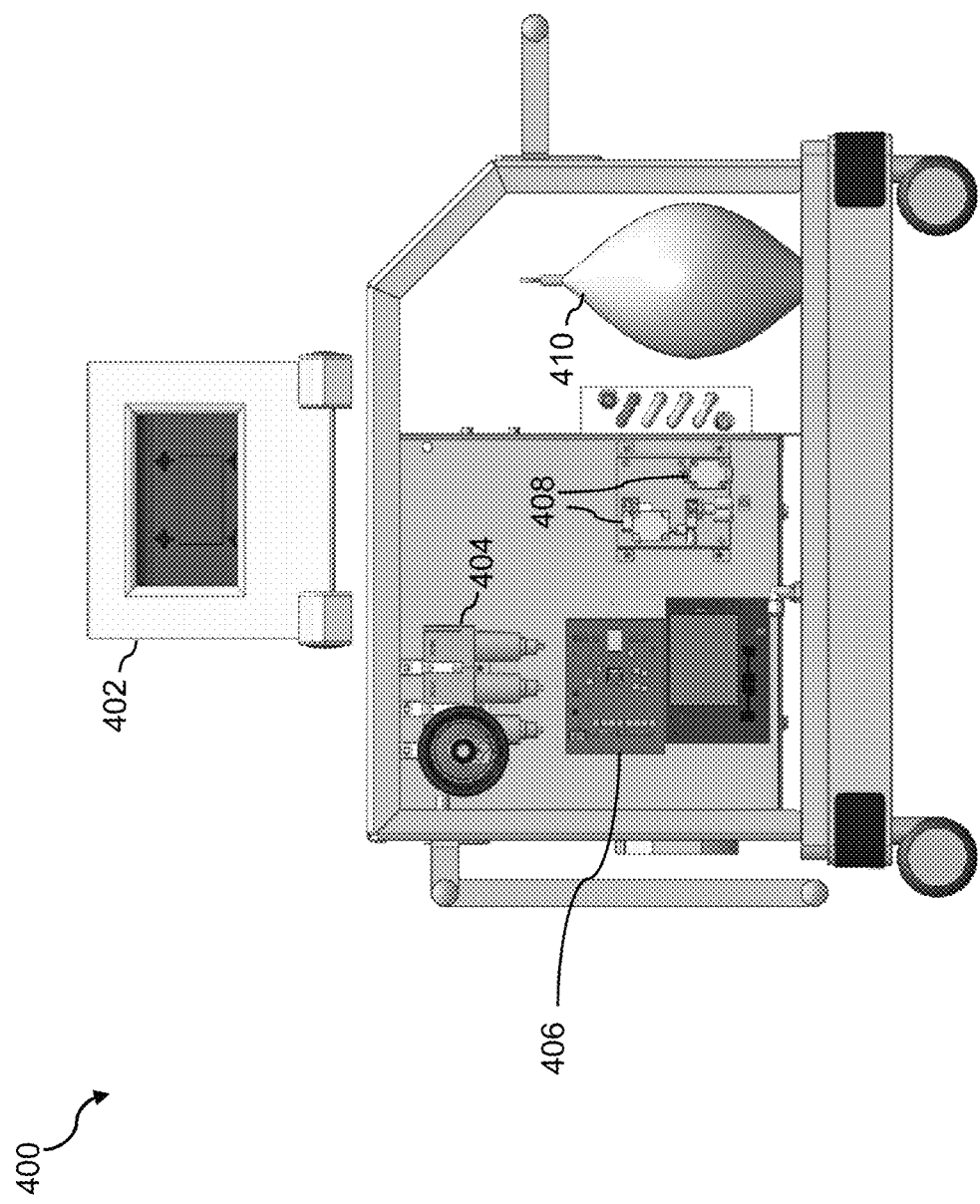
FIG. 4 illustrates a front view of a hypoxic training machine according to an embodiment of the present disclosure.

FIG. 4 illustrates a front view of a hypoxic training machine 400 according to one embodiment of the disclosure. In some embodiments, the hypoxic training machine 400 may correspond to the hypoxic training machine 100. In this view, the hypoxic training machine is shown to include a user interface device 402 that corresponds to the user interface 210 of the controller 200. The user interface device may include both an output and an input mechanism, and may be implemented as a touch-sensitive screen for displaying information (e.g., the current oxygen ratio of the gas being provided to the user, a current detected $SPO^2$ level of the user, an elapsed time since the beginning of a training session, etc.) and for enabling the user or a technician to provide input (e.g., the target $SPO^2$ level, duration of the training session, etc.) to the hypoxic training machine 400. The hypoxic training machine 400 is also shown to include one or more filters 404 that correspond to the filters 106 of the hypoxic training machine 100. The hypoxic training machine 400 is also shown to include a circuit board 406 that corresponds to the controller 110 and/or 200. In some embodiments, the circuit board 406 includes a hardware processor and a non-transitory memory. In addition, the hypoxic training machine 400 is also shown to include solenoids 408 that correspond to the solenoids 122 and 124 of the gas processor 108, and a 3-liter air bag 410 that corresponds to the overflow bag 112.

Figure 5:
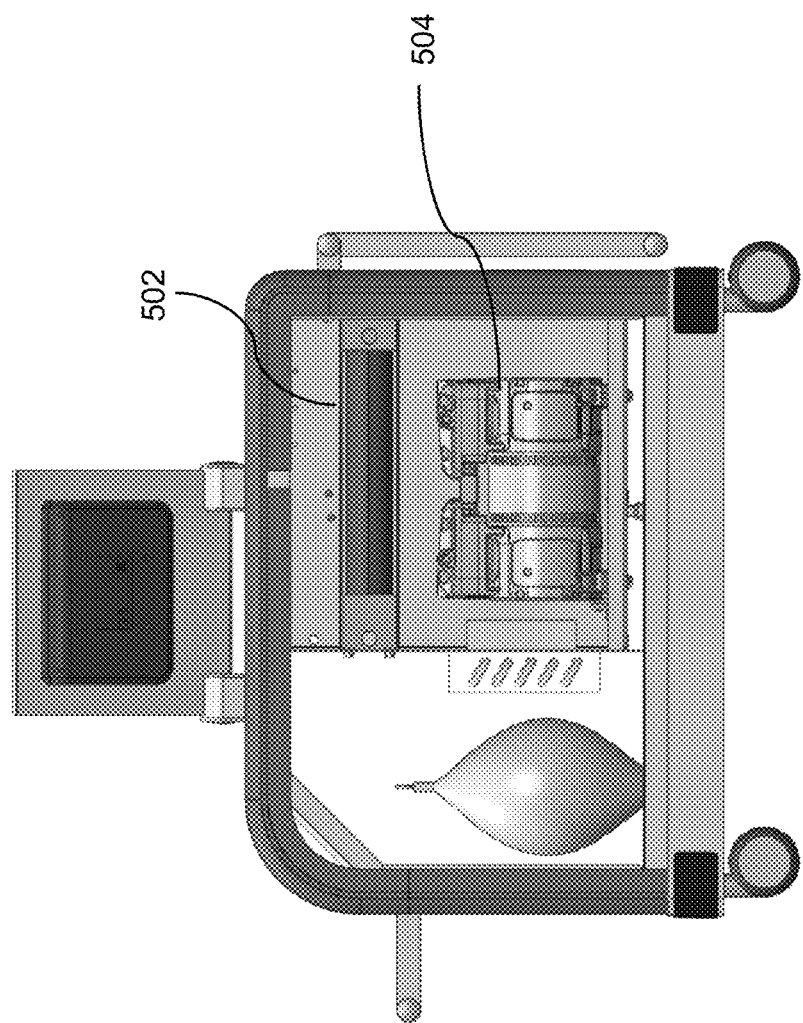
FIG. 5 illustrates a back view of a hypoxic training machine according to an embodiment of the present disclosure.

FIG. 5 illustrates a back view of the hypoxic training machine 400 according to one embodiment of the disclosure. In this view, the hypoxic training machine 400 is shown to include an air compressor 502 that corresponds to the compressor 102 of the hypoxic training machine 100 and a membrane 504 that corresponds to the membrane 120 of the gas processor 108.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software in accordance with the present disclosure, such as program code and/or data, may be stored on one or more non-transitory computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

The various features and steps described herein may be implemented as systems comprising one or more memories storing various information described herein and one or more processors coupled to the one or more memories and a network, wherein the one or more processors are operable to perform steps as described herein, as non-transitory machine-readable medium comprising a plurality of machine-readable instructions which, when executed by one or more processors, are adapted to cause the one or more processors to perform a method comprising steps described herein, and methods performed by one or more devices, such as a hardware processor, user device, server, and other devices described herein.

What is claimed is:

1. A hypoxic training apparatus, comprising:
   a gas processor configured to produce gas according to a given oxygen ratio and to provide processed gas to an outlet junction; and
   a controller communicatively coupled with the gas processor and configured to:
      control the gas processor to produce first gas according to a first training oxygen ratio during a first training period;
      determine, based on one or more first readings from a pulse oximeter, that a blood oxygen saturation level of a subject has fallen to a first predetermined blood saturation level during the first training period;
      in response to determining that the blood oxygen saturation level of the subject has fallen to the first predetermined blood saturation level during the first training period, control the gas processor to produce second gas according to a normoxic oxygen ratio during a first recovery period;
      determine, based on one or more second readings from the pulse oximeter, that the blood oxygen saturation level of the subject has fallen more than a predetermined threshold below the first predetermined blood saturation level during the first recovery period;
      in response to determining that the blood oxygen saturation level of the subject has fallen more than the predetermined threshold below the first predetermined blood saturation level during the first recovery period, determine a second training oxygen ratio for a second training period based on increasing the first training oxygen ratio; and
      in response to determining that the blood oxygen saturation level of the subject has risen to a second predetermined blood saturation level higher than the first predetermined blood saturation level during the first recovery period, control the gas processor to produce third gas according to the second training oxygen ratio during the second training period.

2. The apparatus of claim 1, further comprising a mask coupled with the outlet junction and configured to provide the subject with the processed gas.

3. The apparatus of claim 1, further comprising the pulse oximeter.

4. The apparatus of claim 1, wherein the normoxic oxygen ratio is an oxygen ratio within a range between 20% and 22%, inclusively.

5. The apparatus of claim 1, wherein the first training oxygen ratio is lower than the normoxic oxygen ratio.

6. The apparatus of claim 1, wherein the first training oxygen ratio is a ratio within a range between 7% and 19%, inclusively.

7. The apparatus of claim 1, wherein the predetermined threshold is a percentage within a range between 1% and 4%, inclusively.

8. The apparatus of claim 1, wherein the predetermined threshold is a percentage within a range between 1.5% and 3%, inclusively.

9. The apparatus of claim 1, wherein the second predetermined blood saturation level is between the 100% and the first predetermined blood saturation level.

10. The apparatus of claim 1, wherein the second training oxygen ratio is larger than the first training oxygen ratio by a predetermined value within a range between 0.2% and 1.5%, inclusively.

11. The apparatus of claim 1, wherein the controller is further configured to:
    determine, based on one or more third readings from the pulse oximeter, the blood oxygen saturation level of the subject has reached the first predetermined blood saturation level during the second training period; and
    in response to determining that the blood oxygen saturation level of the subject has reached the first predetermined blood saturation level during the second training period, control the gas processor to produce fourth gas at the normoxic oxygen ratio during a second recovery period.

12. The apparatus of claim 11, wherein the controller is further configured to:
    in response to determining that the blood oxygen saturation level of the subject has not fallen more than the predetermined threshold below the first predetermined blood saturation level during the second recovery period, control the gas processor to produce fifth gas according to the first training oxygen ratio during a third training period.

13. The apparatus of claim 1, wherein the controller is further configured to:
    in response to determining that the blood oxygen saturation level of the subject has not reached the first predetermined blood saturation level during the second training period, control the gas processor to produce fourth gas at a third training oxygen ratio lower than the second training oxygen ratio during a third training period.

14. The apparatus of claim 1, wherein the gas processor comprises a membrane configured to receive a gas input and reduce an oxygen content of the gas input.

15. The apparatus of claim 14, wherein the gas processor further comprises a solenoid having an adjustable flow guide downstream to the membrane and configured to produce a back pressure for the membrane.

16. The apparatus of claim 1, further comprising a compressor disposed upstream of the gas processor and configured to provide compressed air to the gas processor.

17. A method for providing an intermittent hypoxic training, the method comprising:
    controlling, by one or more hardware processors, a gas processor to produce first gas according to a first training oxygen ratio during a first training period, wherein the first gas is provided to a subject;
    determining, by the one or more hardware processors and based on one or more first readings from a pulse oximeter, that a blood oxygen saturation level of the subject has reached a first predetermined blood saturation level during the first training period;
    in response to determining that the blood oxygen saturation level of the subject has reached the first predetermined blood saturation level during the first time period, controlling, by the one or more hardware processors, the gas processor to produce second gas according to a normoxic oxygen ratio during a first recovery period;

determining, by the one or more hardware processors and based on one or more second readings from the pulse oximeter, that the blood oxygen saturation level of the subject has fallen more than a predetermined threshold below the first predetermined blood saturation level during the first recovery period;

in response to determining that the blood oxygen saturation level of the subject has fallen more than the predetermined threshold below the first predetermined blood saturation level during the first recovery period, determining a second training oxygen ratio for a second training period based on increasing, by the one or more hardware processors, the first training oxygen ratio; and in response to determining that the blood oxygen saturation level of the subject has reached a second predetermined blood saturation level higher than the first predetermined blood saturation level during the first recovery period, controlling, by the one or more hardware processors, the gas processor to produce third gas according to the second training oxygen ratio during the second training period.

18. The method of claim 17, wherein the predetermined threshold is a percentage within a range between 1.5% and 3%, inclusively.

19. The method of claim 17, wherein the second training oxygen ratio is larger than the first training oxygen ratio by a predetermined value within a range between 0.2% and 1.5%, inclusively.

20. The method of claim 17, further comprising:
in response to determining that the blood oxygen saturation level of the subject has not reached the first predetermined blood saturation level during the second training period, control the gas processor to produce fourth gas at a third training oxygen ratio lower than the second training oxygen ratio during a third training period.

* * * * *